US012240904B2

(12) United States Patent
Zhang et al.

(10) Patent No.: US 12,240,904 B2
(45) Date of Patent: Mar. 4, 2025

(54) USE OF ANTI-PD-1 ANTIBODY IN COMBINATION WITH FAMITINIB IN PREPARATION OF DRUG FOR TREATING TUMORS

(71) Applicants: Jiangsu Hengrui Medicine Co., Ltd., Jiangsu (CN); Suzhou Suncadia Biopharmaceuticals Co., Ltd., Jiangsu (CN)

(72) Inventors: Lianshan Zhang, Jiangsu (CN); Qing Yang, Jiangsu (CN); Quanren Wang, Jiangsu (CN); Xiaoxing Huang, Jiangsu (CN); Cheng Liao, Jiangsu (CN); Changyong Yang, Jiangsu (CN); Dingwei Ye, Jiangsu (CN); Xiaohua Wu, Jiangsu (CN)

(73) Assignees: Jiangsu Hengrui Medicine Co., Ltd., Jiangsu (CN); Suzhou Suncadia Biopharmaceuticals Co., Ltd., Jiangsu (CN)

( * ) Notice: Subject to any disclaimer, the term of this patent is extended or adjusted under 35 U.S.C. 154(b) by 965 days.

(21) Appl. No.: 17/288,894

(22) PCT Filed: Nov. 5, 2019

(86) PCT No.: PCT/CN2019/115608
§ 371 (c)(1),
(2) Date: Apr. 26, 2021

(87) PCT Pub. No.: WO2020/093993
PCT Pub. Date: May 14, 2020

(65) Prior Publication Data
US 2022/0251203 A1 Aug. 11, 2022

(30) Foreign Application Priority Data
Nov. 6, 2018 (CN) .......................... 201811313004.X

(51) Int. Cl.
*C07K 16/28* (2006.01)
*A61K 31/437* (2006.01)
*A61K 39/00* (2006.01)
*A61P 35/00* (2006.01)

(52) U.S. Cl.
CPC ........ *C07K 16/2818* (2013.01); *A61K 31/437* (2013.01); *A61P 35/00* (2018.01); *A61K 2039/505* (2013.01)

(58) Field of Classification Search
CPC .................. C07K 16/2818; A61P 35/00; A61K 2039/505
See application file for complete search history.

(56) References Cited

U.S. PATENT DOCUMENTS

| 10,344,090 B2 | 7/2019 | Yuan et al. | |
| 11,208,484 B2 * | 12/2021 | Sun | A61K 39/3955 |
| 11,866,500 B2 * | 1/2024 | Sun | C07K 16/2818 |

FOREIGN PATENT DOCUMENTS

| CA | 3038586 A1 * | 4/2018 | ........... A61K 31/444 |
| CN | 108079292 A | 5/2018 | |
| CN | 109893654 A | 6/2019 | |
| WO | 2007085188 A1 | 8/2007 | |
| WO | 2015085847 A1 | 6/2015 | |
| WO | WO-2015119930 A1 * | 8/2015 | ......... A61K 31/4439 |
| WO | WO-2017054646 A1 * | 4/2017 | ........... A61K 39/395 |
| WO | WO-2018068691 A1 * | 4/2018 | ........... A61K 31/444 |
| WO | 2018160841 A1 | 9/2018 | |

OTHER PUBLICATIONS

Ge et al. Famitinib exerted powerful antitumor activity in human gastric cancer cells and xenografts. Oncol Lett. 2016. 12:1763-1768. (Year: 2016).*
Xie et al. Metabolism and bioactivation of famitinib, a novel inhibitor of receptor tyrosine kinase, in cancer patients. Br J Pharmacol. 2013. 168:1687-1706. (Year: 2013).*
Cao et al. Hypothyroidism as a potential biomarker of efficacy of famitinib, a novel VEGFR-2 inhibitor in metastatic breast cancer. Cancer Chemother Pharmacol. 2014. 74:389-398. (Year: 2014).*
Park et al. Vascular Ehlers-Danlos syndrome with cryptorchidism, recurrent pneumothorax, and pulmonary capillary hemangiomatosis-like foci. Medicine. 2017. 96(47): 1-7. (Year: 2017).*
Written Opinion of the International Searching Authority; China National Intellectual Property Administration; International Application No. PCT/CN2019/115608; Feb. 26, 2020; 12 pages.
International Preliminary Report on Patentability; The International Bureau of WIPO; International Application No. PCT/CN2019/115608; May 11, 2021; 13 pages.
International Search Report; China National Intellectual Property Administration; International Application No. PCT/CN2019/115608; Feb. 26, 2020; 10 pages.
Hodi, Stephen F. et al.; Improved Survival with Ipilimumab in Patients with Metastatic Melanoma; The New England Journal of Medicine; Aug. 19, 2010; pp. 711-723; vol. 363; No. 8; Massachusetts Medical Society.

* cited by examiner

*Primary Examiner* — Daniel E Kolker
*Assistant Examiner* — Maureen Varina Driscoll
(74) *Attorney, Agent, or Firm* — Taft Stettinius & Hollister LLP

(57) ABSTRACT

The present disclosure provides the use of an anti-PD-1 antibody in combination with famitinib in the preparation of a drug for treating tumors. In the present technical solution, toxicity is controllable and tolerable. At the same time, the described drug combination effectively reduces adverse reactions to the anti-PD-1 antibody, such as the occurrence of reactive capillary endothelial proliferation.

16 Claims, No Drawings
Specification includes a Sequence Listing.

USE OF ANTI-PD-1 ANTIBODY IN COMBINATION WITH FAMITINIB IN PREPARATION OF DRUG FOR TREATING TUMORS

CROSS-REFERENCE TO RELATED APPLICATIONS

This application is a U.S. National Phase of International PCT Application No. PCT/CN2019/115608 filed Nov. 5, 2019, which claims priority to Chinese Patent Application Serial No. 201811313004.X filed Nov. 6, 2018, the contents of each application are incorporated herein by reference in their entirety.

SEQUENCE LISTING

This application incorporates by reference the material in the ASCII text file titled Amended Sequence Listing.txt, which was created on Oct. 14, 2021 and is 10 KB.

FIELD OF THE INVENTION

The present disclosure relates to use of an anti-PD-1 antibody in combination with famitinib or a pharmaceutically acceptable salt thereof in the preparation of a medicament for the treatment of tumors.

BACKGROUND OF THE INVENTION

There are various genetic and epigenetic changes in cancers, resulting in new antigens that can be recognized by the immune system. Adaptive immune system, including T and B lymphocytes, has a strong anti-cancer potential, extensive capability and fine specificity to respond to various tumor antigens. In addition, the immune system exhibits considerable plasticity and memory components. Successful use of all these properties of the adaptive immune system will make immunotherapy unique among all treatment means for cancers.

Immunotherapy for cancers has focused on methods of enhancing the immune response to tumors through adoptive transfer of activated effector cells, immunity against related antigens or the provision of non-specific immunostimulants, such as cytokines. In recent years, the development of inhibitors specific for immune checkpoint pathway has become a new immunotherapeutic method for the treatment of cancers, such as Ipilimumab (YERVOY®), a CTLA antibody, for the treatment of advanced melanoma (Hodi et al., 2010), nivolumab or pembrolizumab, specifically binding to the programmed death receptor (PD-1), and the like.

PD-1 antibodies specifically recognize and bind to PD-1 present on the surface of lymphocytes, block the PD-1/PD-L1 signaling pathway, thereby activate the effects of immune T cells to kill the tumors, and mobilize the body's immune system to eliminate tumor cells in the body. WO2015085847 discloses a new anti-PD-1 antibody. The PD-1 antibody is currently at the stage of clinical trials and has shown a certain anti-tumor effect.

In a multicenter randomized double-blind placebo-controlled phase II trial of advanced/metastatic colorectal adenocancer in which second-line or above second-line standard chemotherapy of famitinib has failed, famitinib group (25 mg, once a day, for a period of 42 days) improves the progression-free survival (PFS) of patients with advanced/metastatic colorectal cancer, when compared to the placebo group by 1.3 months (HR is 0.596, P is 0.0053). The objective remission rate (ORR) is 2.2%, the disease control rate (DCR) is 59.8%, the median survival (mOS) is 7.5 months, whereas the median survival for placebo group is 7.6 months, and adverse events are under control. The structure is as follows:

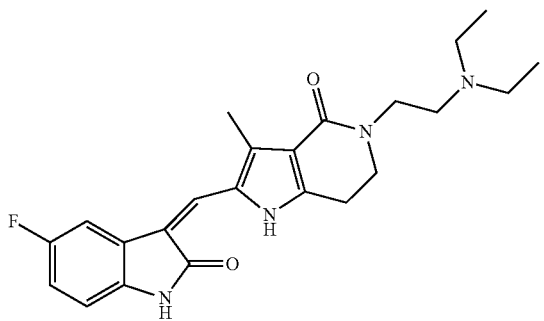 [SMILES: CCN(CC)CCN1CCc2[nH]c(/C=C3\C(=O)Nc4ccc(F)cc43)c(C)c2C1=O]

At present, several combination therapies of the PD-1 antibody and a VEGFR inhibitor (such as sunitinib, sorafenib, etc.) are in clinical phase II/III, and are suitable for malignant liver cancer (sorafenib combined with a PD-1 antibody) and for metastatic renal cell cancer (sunitinib combined with a PD-1 antibody) respectively. The preliminary results show that the combination of the two drugs shows effects superior to a single drug. However, there is no report about the combination of famitinib and a PD-1 antibody.

SUMMARY OF THE INVENTION

The present disclosure provides use of an anti-PD-1 antibody or antigen-binding fragment thereof in combination with famitinib or a pharmaceutically acceptable salt thereof in the preparation of a medicament for the treatment of tumors.

The PD-1 antibody is known, and preferably the light chain variable region of the PD-1 antibody comprises LCDR1, LCDR2 and LCDR3 as shown in SEQ ID NO: 4, SEQ ID NO: 5 and SEQ ID NO: 6 respectively.

The heavy chain variable region of the PD-1 antibody comprises HCDR1, HCDR2 and HCDR3 as shown in SEQ ID NO: 1, SEQ ID NO: 2 and SEQ ID NO: 3 respectively.

Among them, the CDR sequences mentioned above are shown in the following table:

| Name | Sequence | SEQ ID NO: |
|---|---|---|
| HCDR1 | SYMMS | SEQ ID NO: 1 |
| HCDR2 | TISGGGANTYYPDSVKG | SEQ ID NO: 2 |
| HCDR3 | QLYYFDY | SEQ ID NO: 3 |
| LCDR1 | LASQTIGTWLT | SEQ ID NO: 4 |
| LCDR2 | TATSLAD | SEQ ID NO: 5 |
| LCDR3 | QQVYSIPWT | SEQ ID NO: 6 |

Preferably, the PD-1 antibody is a humanized antibody.

In some embodiments, the humanized antibody comprises a light chain variable region as shown in SEQ ID NO: 10 or variant thereof, and the variant preferably has 0-10 amino acid change(s), more preferably A43S amino acid change, on the light chain variable region of SEQ ID NO: 10; and the humanized antibody comprises a heavy chain variable region as shown in SEQ ID NO: 9 or variant thereof, and the variant preferably has 0-10 amino acid change(s), more preferably G44R amino acid change, on the heavy chain variable region of SEQ ID NO: 9.

The sequences of the heavy and light chain variable regions of the aforementioned humanized antibody are as follows:

```
Heavy chain variable region
                                         SEQ ID NO: 9
EVQLVESGGGLVQPGGSLRLSCAASGFTFSSYMMSWVRQAPGKGLEWVAT

ISGGGANTYYPDSVKGRFTISRDNAKNSLYLQMNSLRAEDTAVYYCARQL

YYFDYWGQGTTVTVSS;

Light chain variable region
                                        SEQ ID NO: 10
DIQMTQSPSSLSASVGDRVTITCLASQTIGTWLTWYQQKPGKAPKLLIYT

ATSLADGVPSRFSGSGSGTDFTLTISSLQPEDFATYYCQQVYSIPWTFGG

GTKVEIK.
```

In other embodiments, the humanized antibody comprises a light chain as shown in SEQ ID NO: 8 or variant thereof, and the variant preferably has 0-10 amino acid change(s), more preferably A43S amino acid change, on the light chain variable region; and the humanized antibody comprises a heavy chain as shown in SEQ ID NO: 7 or variant thereof, and the variant preferably has 0-10 amino acid change(s), more preferably G44R amino acid change, on the heavy chain variable region.

In another embodiment, the humanized antibody comprises a light chain as shown in SEQ ID NO: 8 and a heavy chain as shown in SEQ ID NO: 7.

The sequences of the heavy and light chains of the humanized antibody are as follows:

```
Heavy chain
                                         SEQ ID NO: 7
EVQLVESGGGLVQPGGSLRLSCAASGFTFSSYMMSWVRQAPGKGLEWVAT

ISGGGANTYYPDSVKGRFTISRDNAKNSLYLQMNSLRAEDTAVYYCARQL

YYFDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK;

Light chain
                                         SEQ ID NO: 8
DIQMTQSPSSLSASVGDRVTITCLASQTIGTWLTWYQQKPGKAPKLLIYT

ATSLADGVPSRFSGSGSGTDFTLTISSLQPEDFATYYCQQVYSIPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

The anti-PD-1 antibody or antigen-binding fragment thereof combined with famitinib or a pharmaceutically acceptable salt thereof disclosed herein has a synergistic effect.

The use according to the present disclosure, based on the body weight of the patient, the anti-PD-1 antibody or antigen-binding fragment thereof is administered to a human subject at a dose ranging from 0.1 to 10.0 mg/kg, which may be 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.2 mg/kg, 1.4 mg/kg, 1.6 mg/kg, 1.8 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, 4.0 mg/kg, 4.2 mg/kg, 4.4 mg/kg, 4.6 mg/kg, 4.8 mg/kg, 5.0 mg/kg, 5.2 mg/kg, 5.4 mg/kg, 5.6 mg/kg, 5.8 mg/kg, 6.0 mg/kg, 6.2 mg/kg, 6.4 mg/kg, 6.6 mg/kg, 6.8 mg/kg, 7.0 mg/kg, 7.2 mg/kg, 7.4 mg/kg, 7.6 mg/kg, 7.8 mg/kg, 8.0 mg/kg, 8.2 mg/kg, 8.4 mg/kg, 8.6 mg/kg, 8.8 mg/kg, 9.0 mg/kg, 9.2 mg/kg, 9.4 mg/kg, 9.6 mg/kg, 9.8 mg/kg, 10.0 mg/kg, or any value between any two values.

In an alternative embodiment, the PD-1 antibody or antigen-binding fragment thereof is administered to a human subject at a dose ranging from 10 to 300 mg, which may be 10.0 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, or any value between any two values, preferably 50-300 mg, most preferably 200 mg.

The anti-PD-1 antibody or antigen-binding fragment thereof of the present disclosure is administered at a frequency of once a day, once every two days, once every three days, once every four days, once every five days, once every six days, once a week, once every two weeks, once every three weeks, once every four weeks, or once a month, preferably once every three weeks.

In an alternative embodiment, the anti-PD-1 antibody or antigen-binding fragment thereof of the present disclosure is administered at a dose ranging from 50 to 300 mg once every 2-3 weeks, more preferably 200 mg once every 2-3 weeks.

The use according to the present disclosure, based on the body weight of the patient, the famitinib or the pharmaceutically acceptable salt thereof is administered to a human subject at a dose ranging from 0.1 to 10.0 mg/kg, which may be 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.2 mg/kg, 1.4 mg/kg, 1.6 mg/kg, 1.8 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, 4.0 mg/kg, 4.2 mg/kg, 4.4 mg/kg, 4.6 mg/kg, 4.8 mg/kg, 5.0 mg/kg, 5.2 mg/kg, 5.4 mg/kg, 5.6 mg/kg, 5.8 mg/kg, 6.0 mg/kg, 6.2 mg/kg, 6.4 mg/kg, 6.6 mg/kg, 6.8 mg/kg, 7.0 mg/kg, 7.2 mg/kg, 7.4 mg/kg, 7.6 mg/kg, 7.8 mg/kg, 8.0 mg/kg, 8.2 mg/kg, 8.4 mg/kg, 8.6 mg/kg, 8.8 mg/kg, 9.0 mg/kg, 9.2 mg/kg, 9.4 mg/kg, 9.6 mg/kg, 9.8 mg/kg, 10.0 mg/kg, or any value between any two values.

In an alternative embodiment, the famitinib or the pharmaceutically acceptable salt thereof is administered to a human subject at a dose ranging from 0.1 to 100 mg, which may be 0.1 mg, 0.2 mg, 0.3 mg, 0.4 mg, 0.5 mg, 0.6 mg, 0.7 mg, 0.8 mg, 0.9 mg, 1.0 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, or any value between any two values, preferably 1-20 mg.

The use of the present disclosure, wherein the famitinib or the pharmaceutically acceptable salt thereof is administered at a frequency of once a day; once every two days; once every three days; once every four days; once every five days; once every six days; once a week; once a day, for three days every week; once a day, for four days every week; once a day, for five days every week.

In an alternative embodiment, the anti-PD-1 antibody or antigen-binding fragment thereof is administered to a human subject at a dose ranging from 10 to 300 mg, and the famitinib or the pharmaceutically acceptable salt thereof is administered to a human subject at a dose ranging from 0.1 to 100 mg.

In an alternative embodiment, the anti-PD-1 antibody or antigen-binding fragment thereof is administered to a human subject at a dose ranging from 10 to 300 mg, once every 2-3 weeks, and the famitinib or the pharmaceutically acceptable salt thereof is administered to a human subject at a dose ranging from 0.1 to 100 mg, once a day.

In an alternative embodiment, the anti-PD-1 antibody or antigen-binding fragment thereof is administered to a human subject at a dose ranging from 50 to 300 mg, and the famitinib or the pharmaceutically acceptable salt thereof is administered to a human subject at a dose ranging from 1 to 20 mg.

In an alternative embodiment, the anti-PD-1 antibody or antigen-binding fragment thereof is administered to a human subject at a dose ranging from 50 to 300 mg, once every 2-3 weeks, and the famitinib or the pharmaceutically acceptable salt thereof is administered to a human subject at a dose ranging from 1 to 20 mg, once a day.

In an alternative embodiment, the anti-PD-1 antibody or antigen-binding fragment thereof is administered to a human subject at a dose of 200 mg, and the famitinib or the pharmaceutically acceptable salt thereof is administered to a human subject at a dose ranging from 1 to 20 mg.

In an alternative embodiment, the anti-PD-1 antibody or antigen-binding fragment thereof is administered to a human subject at a dose of 200 mg, once every 2-3 weeks, and the famitinib or the pharmaceutically acceptable salt thereof is administered to a human subject at a dose ranging from 1 to 20 mg, once a day.

In an alternative embodiment, the anti-PD-1 antibody or antigen-binding fragment thereof is administered to a human subject at a dose of 200 mg, once every 3 weeks, and the famitinib or the pharmaceutically acceptable salt thereof is administered to a human subject at a dose ranging from 1 to 20 mg, once a day.

On another aspect, in an alternative embodiment, in the use of the present disclosure, the AUC of famitinib or a pharmaceutically acceptable salt thereof is increased by at least 15% (including 15%, 16%, 17%, 18%, 19%, 20%, 21%, 22%, 23%, 24%, 25%, 26%, 27%, 28%, 29%, 30% or higher), preferably at least 20%, and most preferably at least 25%, when compared to that of the same dose of famitinib or a pharmaceutically acceptable salt thereof administered alone.

In an alternative embodiment, in the use of the present disclosure, the $C_{max}$ of famitinib or a pharmaceutically acceptable salt thereof is increased by at least 15% (including 15%, 16%, 17%, 18%, 19%, 20%, 21%, 22%, 23%, 24%, 25%, 26%, 27%, 28%, 29%, 30% or higher), prefer- ably at least 20%, when compared to that of the same dose of famitinib or a pharmaceutically acceptable salt thereof administered alone.

In a preferred embodiment of the present disclosure, the PD-1 antibody is administered by injection, such as subcutaneous or intravenous injection, and the PD-1 antibody is formulated into an injectable form prior to injection. A particularly preferred injectable form of the PD-1 antibody is an injection solution or a lyophilized powder injection, which comprises the PD-1 antibody, a buffer, a stabilizer, and optionally a surfactant. The buffer may be one or more selected from the group consisting of acetate, citrate, succinate and phosphate. The stabilizer may be selected from saccharides or amino acids, preferably disaccharides, such as sucrose, lactose, trehalose, maltose. The surfactant is selected from the group consisting of polyoxyethylene hydrogenated castor oil, glycerin fatty acid ester and polyoxyethylene sorbitan fatty acid ester, preferably, the polyoxyethylene sorbitan fatty acid ester is polysorbate 20, 40, 60 or 80, most preferably is polysorbate 20. The most preferred injectable form of the PD-1 antibody comprises the PD-1 antibody, acetate buffer, trehalose and polysorbate 20.

The present disclosure provides the above-mentioned anti-PD-1 antibody in combination with famitinib or pharmaceutically acceptable salt thereof, for use in the preparation of a medicament for treating tumors.

The present disclosure provides the above-mentioned anti-PD-1 antibody in combination with famitinib or pharmaceutically acceptable salt thereof, as a medicament for reducing adverse drug reactions. Preferably, the adverse drug reactions are caused by the anti-PD-1 antibody or caused by famitinib or pharmaceutically acceptable salt thereof.

In an alternative embodiment, the adverse reaction described in the use of the present disclosure is preferably an adverse reaction caused by the anti-PD-1 antibody, and most preferably, is reactive capillary hyperplasia.

In some embodiments, the incidence of the reactive capillary hyperplasia is no more than 15% (including 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4%, 4.5%, 3.5%, 3%, 2.5%, 2%, 1.5%, 1% or lower), preferably no more than 2.5%, when compared to the same dose of the anti-PD-1 antibody (such as, the heavy and light chain sequences are shown in SEQ ID No: 7 and SEQ ID NO:8 respectively) administered alone.

The present disclosure provides the above-mentioned anti-PD-1 antibody in combination with famitinib or pharmaceutically acceptable salt thereof, as a medicament for reducing the dose of anti-PD-1 antibody administered alone and/or the dose of famitinib or a pharmaceutically acceptable salt thereof administered alone.

In the present disclosure, a method for treating tumors is provided, which includes administering the above-mentioned anti-PD-1 antibody and famitinib or a pharmaceutically acceptable salt thereof to a patient.

In the present disclosure, provided is a method for reducing the dose of anti-PD-1 antibody administered alone and/or the dose of famitinib or a pharmaceutically acceptable salt thereof administered alone, the method comprising administering the above-mentioned anti-PD-1 antibody in combination with famitinib or a pharmaceutically acceptable salt thereof to a patient.

In other embodiments, when used in combination with PD-1, the famitinib or the pharmaceutically acceptable salt thereof is administered at 10% to 100% (including 10%, 15%, 20%, 30%, 35%, 40%, 45%, 50%, 55%, 60%, 70%, 75%, 80%, 90%, 95%), preferably 10% to 75%, more preferably 75%, 50%, 25%, 12.5% of the dose administered alone.

In other embodiments, when used in combination with famitinib or pharmaceutically acceptable salt thereof, the anti-PD-1 antibody is administered at 10% to 100% (including 10%, 15%, 20%, 30%, 35%, 40%, 45%, 50%, 55%, 60%, 70%, 75%, 80%, 90%, 95%), preferably 10%-50% of the dose administered alone.

The present disclosure also provides a method for reducing adverse reactions caused by the anti-PD-1 antibody or antigen-binding fragment thereof, or by famitinib or pharmaceutically acceptable salt thereof, including administering famitinib or a pharmaceutically acceptable salt thereof in combination with the above-mentioned anti-PD-1 antibody to a patient, and the adverse reaction is preferably an adverse reaction cause by the anti-PD-1 antibody, and most preferably reactive capillary hyperplasia.

In an alternative embodiment, the adverse reaction described in the present disclosure is preferably an adverse reaction caused by the anti-PD-1 antibody, and most preferably, is reactive capillary hyperplasia.

In some embodiments, the incidence of the reactive capillary hyperplasia is no more than 15% (including 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4%, 4.5%, 3.5%, 3%, 2.5%, 2%, 1.5%, 1% or lower), preferably no more than 2.5%, when compared to the same dose of the anti-PD-1 antibody (for example, the heavy and light chain sequences are shown in SEQ ID No: 7 and SEQ ID NO:8 respectively) administered alone.

The present disclosure also provides a pharmaceutical kit, or a pharmaceutical package, or a pharmaceutical combination, which comprises famitinib or pharmaceutically acceptable salt thereof, and a PD-1 antibody.

The present disclosure also provides use of an anti-PD-L1 antibody or anti-CTAL-4 antibody in combination with famitinib or a pharmaceutically acceptable salt thereof in the preparation of a medicament for the treatment of tumors.

In an alternative embodiment, based on the body weight of the patient, the anti-PD-L1 antibody or antigen-binding fragment thereof or the anti-CTAL-4 antibody or antigen-binding fragment thereof is administered to a human subject at a dose ranging from 0.1 to 10.0 mg/kg, which may be 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.2 mg/kg, 1.4 mg/kg, 1.6 mg/kg, 1.8 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, 4.0 mg/kg, 4.2 mg/kg, 4.4 mg/kg, 4.6 mg/kg, 4.8 mg/kg, 5.0 mg/kg, 5.2 mg/kg, 5.4 mg/kg, 5.6 mg/kg, 5.8 mg/kg, 6.0 mg/kg, 6.2 mg/kg, 6.4 mg/kg, 6.6 mg/kg, 6.8 mg/kg, 7.0 mg/kg, 7.2 mg/kg, 7.4 mg/kg, 7.6 mg/kg, 7.8 mg/kg, 8.0 mg/kg, 8.2 mg/kg, 8.4 mg/kg, 8.6 mg/kg, 8.8 mg/kg, 9.0 mg/kg, 9.2 mg/kg, 9.4 mg/kg, 9.6 mg/kg, 9.8 mg/kg, 10.0 mg/kg.

In another alternative embodiment, wherein the anti-PD-L1 antibody or antigen-binding fragment thereof or the anti-CTAL-4 antibody or antigen-binding fragment thereof is administered to a human subject at a dose ranging from 50 to 700 mg, which may be 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, preferably 50 to 600 mg, most preferably 200 mg.

The anti-PD-L1 antibody or antigen-binding fragment thereof or the anti-CTAL-4 antibody or antigen-binding fragment thereof of the present disclosure is administered at a frequency of once a day, once every two days, once every three days, once every four days, once every five days, once every six days, once a week, once every two weeks, once every three weeks, once every four weeks, or once a month.

In an alternative embodiment, the anti-PD-L1 antibody or antigen-binding fragment thereof or the anti-CTAL-4 antibody or antigen-binding fragment thereof described in the present disclosure is administered to a human subject at a dose of 50 to 600 mg, once every 2 to 3 weeks, more preferably 200 mg, once every 2 to 3 weeks.

In an alternative embodiment, the anti-PD-L1 antibody or antigen-binding fragment thereof or the anti-CTAL-4 antibody or antigen-binding fragment thereof is administered to a human subject at a dose ranging from 50 to 700 mg, once every 2-3 weeks, and the famitinib or the pharmaceutically acceptable salt thereof is administered to a human subject at a dose ranging from 0.1 to 100 mg, once a day.

In an alternative embodiment, the anti-PD-L1 antibody or antigen-binding fragment thereof or the anti-CTAL-4 antibody or antigen-binding fragment thereof is administered to a human subject at a dose ranging from 50 to 600 mg, and the famitinib or the pharmaceutically acceptable salt thereof is administered to a human subject at a dose ranging from 1 to 20 mg.

In an alternative embodiment, the anti-PD-L1 antibody or antigen-binding fragment thereof or the anti-CTAL-4 antibody or antigen-binding fragment thereof is administered to a human subject at a dose ranging from 50 to 600 mg, once every 2-3 weeks, and the famitinib or the pharmaceutically acceptable salt thereof is administered to a human subject at a dose ranging from 1 to 20 mg, once a day.

In an alternative embodiment, the anti-PD-L1 antibody or antigen-binding fragment thereof or the anti-CTAL-4 antibody or antigen-binding fragment thereof is administered to a human subject at a dose of 200 mg, and the famitinib or the pharmaceutically acceptable salt thereof is administered to a human subject at a dose ranging from 1 to 20 mg.

In an alternative embodiment, the anti-PD-L1 antibody or antigen-binding fragment thereof or the anti-CTAL-4 antibody or antigen-binding fragment thereof is administered to a human subject at a dose of 200 mg, once every 2-3 weeks, and the famitinib or the pharmaceutically acceptable salt thereof is administered to a human subject at a dose ranging from 1 to 20 mg, once a day.

In a preferred embodiment of the present disclosure, the PD-L1 antibody or the anti-CTAL-4 antibody is administered by injection, such as subcutaneous or intravenous injection, and the PD-L1 antibody or the anti-CTAL-4 antibody is formulated into an injectable form prior to injection.

The present disclosure provides the above-mentioned anti-PD-L1 antibody or the anti-CTAL-4 antibody in combination with famitinib or pharmaceutically acceptable salt thereof, as a medicament for reducing adverse drug reactions. Preferably, the adverse drug reactions are caused by the anti-PD-L1 antibody or the anti-CTAL-4 antibody or caused by famitinib or pharmaceutically acceptable salt thereof.

The present disclosure provides the above-mentioned anti-PD-L1 antibody in combination with famitinib or pharmaceutically acceptable salt thereof, as a medicament for reducing the dose of anti-PD-L1 antibody administered alone and/or famitinib or a pharmaceutically acceptable salt thereof administered alone.

The present disclosure provides the above-mentioned anti-CTAL-4 antibody in combination with famitinib or pharmaceutically acceptable salt thereof, as a medicament for reducing the dose of anti-CTAL-4 antibody administered alone and/or the dose of famitinib or a pharmaceutically acceptable salt thereof administered alone.

In the present disclosure, a method for treating tumors is provided, which includes administering the above-mentioned anti-PD-L1 antibody or anti-CTAL-4 antibody and famitinib or a pharmaceutically acceptable salt thereof to a patient.

In the present disclosure, provided is a method for reducing the dose of anti-PD-L1 antibody administered alone and/or the dose of famitinib or a pharmaceutically acceptable salt thereof administered alone, the method comprising administering the above-mentioned anti-PD-L1 antibody in combination with famitinib or a pharmaceutically acceptable salt thereof to a patient.

In the present disclosure, provided is a method for reducing the dose of anti-CTAL-4 antibody administered alone and/or the dose of famitinib or a pharmaceutically acceptable salt thereof administered alone, the method comprising administering the above-mentioned anti-CTAL-4 antibody in combination with famitinib or a pharmaceutically acceptable salt thereof to a patient.

In an alternative embodiment, when used in combination with PD-L1, the famitinib or the pharmaceutically acceptable salt thereof is administered at 10% to 100% (including 10%, 15%, 20%, 30%, 35%, 40%, 45%, 50%, 55%, 60%, 70%, 75%, 80%, 90%, 95%), preferably 10% to 75%, more preferably 75%, 50%, 25%, 12.5% of the dose administered alone.

In an alternative embodiment, when used in combination with famitinib or pharmaceutically acceptable salt thereof, the dose of the anti-PD-L1 antibody is 10% to 100% (including 10%, 15%, 20%, 30%, 35%, 40%, 45%, 50%, 55%, 60%, 70%, 75%, 80%, 90%, 95%), preferably 10% to 50% of the dose administered alone.

In an alternative embodiment, when used in combination with an anti-CTAL-4 antibody, the dose of the famitinib or the pharmaceutically acceptable salt thereof is 10% to 100%, preferably 10% to 75%, more preferably 75%, 50%, 25%, 12.5% of the dose administered alone.

In an alternative embodiment, when used in combination with famitinib or pharmaceutically acceptable salt thereof, the dose of the anti-CTAL-4 antibody is 10% to 100%, preferably 10% to 50% of the dose administered alone.

The present disclosure also provides a pharmaceutical kit, or a pharmaceutical package, which comprises famitinib or pharmaceutically acceptable salt thereof, and a PD-L1 antibody or an anti-CTAL-4 antibody.

In the use of the present disclosure, the example of the tumor is selected from, but not limited to: breast cancer (such as triple-negative breast cancer), lung cancer, gastric cancer, intestinal cancer (such as rectal cancer, colorectal cancer), kidney cancer (such as renal cell cancer), liver cancer (such as primary liver cancer, hepatocellular cancer, cholangiocancer, metastatic liver cancer, secondary liver cancer), melanoma (such as metastatic melanoma), non-small cell lung cancer, urothelial cancer (such as bladder cancer, ureteral cancer, urethral cancer), cervical cancer, ovarian cancer (such as recurrent ovarian cancer), endometrial cancer, lymphoblastic T-cell leukemia, chronic myeloid leukemia, thyroid cancer, chronic lymphocytic leukemia, hair cell leukemia, acute lymphoblastic leukemia, acute myeloid leukemia (AML), chronic neutrophil leukemia, acute lymphoblastic T-cell leukemia, immunoblast large cell leukemia, mantle cell leukemia, multiple myeloma meganucleus cell leukemia, acute megakaryocytic leukemia, promyelocytic leukemia, erythroleukemia, malignant lymphoma, multiple myeloma, plasmacytoma, Hodgkin's lymphoma, non-Hodgkin's lymphoma, lymphoblastic T-cell lymphoma, Burkitt lymphoma, follicular lymphoma, myelodysplastic syndrome (MDS).

In an alternative embodiment, the tumor according to the use of the present disclosure is non-small cell lung cancer, thyroid cancer, breast cancer (such as triple negative breast cancer), melanoma (e.g., metastatic melanoma), kidney cancer, urothelial cancer (such as bladder cancer, ureteral cancer, urethral cancer), cervical cancer, thyroid cancer, ovarian cancer (e.g., recurrent ovarian cancer), endometrial cancer, intestinal cancer or liver cancer.

In a preferred embodiment, the tumor patient has been treated with platinum-based drugs. For example, the patients who experienced a failed treatment with platinum-based drugs or those who are intolerant to platinum-based drugs, or the diseases that have progressed or relapsed during treatment, or less than 6 months after the treatment with platinum therapy.

In some embodiments, the tumor in the use of the present disclosure is kidney cancer (renal cell cancer). Preferably, the tumor is an advanced renal clear cell cancer (a mixed tumor, such as renal clear cell cancer) diagnosed by histology or cytology.

In a preferred embodiment, the renal cell cancer patient in the use of the present disclosure has been previously treated with interleukin-2 and/or anti-angiogenesis targeted drugs, and the treatment has failed.

In some embodiments, the tumor described in the use of the present disclosure is urothelial cancer (such as bladder cancer, ureteralal cancer, and urethral cancer). Preferably, the tumor is the incurable urothelial cancer (such as renal pelvic cancer, ureteralal cancer, bladder cancer, and urethral cancer, and mixed types of cancer such as transitional cell cancer subtype by histology) diagnosed by histology or cytology.

In a preferred embodiment, the urothelial cancer patient in the use of the present disclosure has been treated with platinum-based drugs. For example, the patients who experienced a failed treatment with platinum-based drugs or those who are intolerant to platinum-based drugs, or the diseases that have progressed or relapsed during, or after the treatment with platinum therapy.

In some embodiments, the tumor in the use of the present disclosure is cervical cancer. Preferably, the tumor is advanced cervical squamous cell cancer diagnosed by histology or cytology.

In a preferred embodiment, the therapy of cervical cancer by using previous ≥1 line system in a patient has failed.

In other embodiments, the tumor in the use of the present disclosure is ovarian cancer, preferably, recurrent ovarian cancer, and further, recurrent ovarian epithelial cancer, fallopian tube cancer or primary peritoneal cancer diagnosed by histopathology.

In a preferred embodiment, the recurrent ovarian cancer patient has been treated with platinum-based drugs. For example, the patients who experienced a failed treatment with platinum-based drugs or those who are intolerant to platinum-based drugs, or the diseases that have progressed or relapsed during treatment, or less than 6 months after the treatment with platinum therapy (finished 4 or more courses of treatment).

In some other embodiments, the tumor in the use of the present disclosure is endometrial cancer, preferably, endometrial cancer diagnosed by histopathology. In a preferred embodiment, the endometrial cancer patient has been treated with platinum-based drugs. For example, the patients who experienced a failed treatment with platinum-based drugs or those who are intolerant to platinum-based drugs, or the diseases that have progressed or relapsed during treatment, or less than 6 months after the treatment with platinum therapy (finished 4 or more courses of treatment).

The present disclosure also provides use of famitinib or a pharmaceutically acceptable salt thereof in the preparation of a medicament for the treatment of a disorder which would receive benefit from the inhibition of TYRO3 and/or AXL and/or MER.

The present disclosure also provides a method for treating a disorder which would receive benefit the inhibition of TYRO3 and/or AXL and/or MER with famitinib or a pharmaceutically acceptable salt thereof, which comprises administering the above famitinib or the pharmaceutically acceptable salt thereof to a patient. Further, in an alternative embodiment, the famitinib or the pharmaceutically acceptable salt thereof can be used alone or in combination.

Further, in an alternative embodiment, the famitinib or the pharmaceutically acceptable salt thereof can be administered alone or in combination.

Examples of the disorder which would receive benefit from the inhibition of TYRO3 (Tyro3 tyrosine kinase receptor inhibitor) and/or AXL (Axl tyrosine kinase receptor inhibitor) and/or MER (Mer tyrosine kinase receptor inhibitor) described in this disclosure include but are not limited to: lymphoblastic T-cell leukemia, chronic myeloid leukemia, chronic lymphocytic leukemia, hair cell leukemia, acute lymphoblastic leukemia, acute myeloid leukemia (AML), chronic neutrophil leukemia, acute lymphoblastic T-cell leukemia, immunoblast large cell leukemia, mantle cell leukemia, multiple myeloma meganucleus cell leukemia, acute megakaryocytic leukemia, promyelocytic leukemia, erythroleukemia, malignant lymphoma, multiple myeloma, plasmacytoma, Hodgkin's lymphoma, non-Hodgkin's lymphoma, lymphoblastic T-cell lymphoma, Burkitt lymphoma, follicular lymphoma, myelodysplastic syndrome (MDS), thrombotic disorders (such as myocardial infarction, ischemic cerebral infarction, peripheral vascular disease, venous thromboembolism, etc.), etc.

The pharmaceutically acceptable salt of famitinib in the present disclosure is selected from but not limited to methanesulfonate, maleate, tartrate, succinate, acetate, difluoroacetate, fumarate, citrate, benzenesulfonate, benzoate, naphthalenesulfonate, lactate, malate, hydrochloride, hydrobromide, sulfate and phosphate, preferably malate.

In some embodiments of the present disclosure, the pharmaceutically acceptable salt of famitinib is administered to a human subject at a dose calculated based its form of free base.

Without explanation to the contrary, the terms in this disclosure are defined as follows:

In the present disclosure, "AUC" refers to the area surrounded by the pharmacokinetic blood drug concentration curve versus time axis. This parameter is an important indicator for evaluating the degree of drug absorption, reflecting the exposure profiles of the drug in vivo. Since the blood drug concentration in pharmacokinetic studies can only be observed up to a certain time point t, AUC can be expressed in the following two means: AUC (0-t) and AUC (0-∞), wherein AUC (0-t) is derived from the trapezoidal area, and AUC (0-∞) is calculated by the formula: AUC (0-∞)=AUC (0-t)+end point concentration/end point elimination rate. The AUC mentioned in the present application refers to the averaged AUC0-24 of the patient reaching a steady state after a single administration or multiple administrations, preferably the averaged AUC0-24 of the patient reaching a steady state after multiple administrations (i.e. $AUC_{ss}$).

In the present disclosure, "combination" refers to a mode of administration; it means that at least one dose of famitinib or a pharmaceutically acceptable salt, and at least one dose of anti-PD-1 antibody or antigen binding fragment thereof are administered within a certain period of time, wherein both substances show pharmacological effects. The time period may be within one administration cycle, preferably within 4 weeks, within 3 weeks, within 2 weeks, within 1 week, or within 24 hours. Famitinib or a pharmaceutically acceptable salt thereof can be administered simultaneously or sequentially along with the anti-PD-1 antibody or antigen-binding fragment thereof. This time period includes such treatments in which famitinib or a pharmaceutically acceptable salt is administered with the anti-PD-1 antibody or antigen-binding fragment thereof through the same or different administration routes. The combined administration mode of the present disclosure is selected from the group consisting of simultaneous administration, co-administration of separate formulations, and sequential administration of separate formulations. Overall survival (OS) refers to the period starting from a random time to death due to any cause. For subjects who are still alive at the last follow-up, the last time for follow-up is recorded as censored data for OS. For subjects who are lost to follow-up, the last time when the subject can be confirmed as being alive is recorded as censored data for OS. The OS with censored data is defined as the period starting from the time of random grouping to the time of censoring data.

Objective remission rate (Objective response rate, ORR) refers to the proportion of patients whose tumors have shrunk to a certain level and maintained for a certain period of time, including CR and PR cases. The solid tumor response assessment standard (RECIST 1.1 standard) was used to assess the objective remission of tumor. Subjects must be accompanied by measurable tumor lesions at baseline. For the efficacy evaluation standard, efficacy can be classified into complete remission (CR), partial remission (PR), stable disease (SD), and progress disease (PD) according to the RECIST 1.1 standard.

Disease Control Rate (DCR) refers to the percentage of the numbers of cases showing confirmed complete remission, partial remission, and stable disease (≥8 weeks) to the numbers of patients for whom the therapeutic efficacy is evaluable.

Complete remission (CR): All target lesions disappear, and the shorter diameter of all pathological lymph nodes (including target and non-target nodules) must be reduced to <10 mm.

Partial remission (PR): The sum of the diameters of the target lesions is reduced by at least 30% from the baseline level.

Progression Disease (PD): The sum of diameters for all target lesions is increased by at least 20%, when compared to the minimum value of the sum of diameters (as the reference), measured during the entire experimental study (the sum of diameters for all target lesions measured at baseline would be served as the reference, if it is the minimum value); In addition, the absolute value of the sum of diameters must be increased by at least 5 mm (the development of one or more new lesions is also regarded as progression disease).

Stable disease (SD): the reduced degree of the target lesions does not reach PR, and the increase degree does not reach PD level, a status between PR and PD. The minimum value of the sum of diameters can be used as the reference during the study.

"mpk": mg/kg.

The reagents, biological samples or active agents used in the present disclosure are commercially available, for example, human PD-1 transgenic mice, 4-5 weeks-old, were purchased from Cephrim Biosciences, Inc. UK.

DETAILED DESCRIPTION OF THE INVENTION

The following examples are provided to further describe the present disclosure, but are not intended to limit the scope of the disclosure.

Example 1

Human PD-1 transgenic mice were used as test animals, and the efficiency of co-administration of PD-1 antibodies and famitinib was evaluated in human PD-1 transgenic mice with transplanted tumor C57 of mouse colon cancer cells MC-38 (PD-L1).

Compound A: PD-1 antibody with heavy and light chain sequences as shown in SEQ ID NO: 7 and SEQ ID NO: 8 of the present disclosure. 200 mg/each vial, formulated as 20 mg/ml for use.

Compound B: famitinib malate, which was prepared according to the method in patent application WO2007085188.

Test Protocol:

On day 7, MC38 cells (5×10⁵) were subcutaneously inoculated into 40 human PD-1 transgenic mice (including male and female) at right flank. When the average tumor volume of the mice reached about 100 mm³, 32 mice were selected and randomly divided into 4 groups, 8 mice in each group. After grouping, mice were given vehicle control, intraperitoneal injection of compound A, oral gavage of compound and co-administration of both according to the protocol. The tumor volume was measured twice a week, the mice were weighed, and the data was recorded.

| Group No. | Grouping | Number of animals | Dose (mg/kg) | Dosing frequency | Route of administration |
|---|---|---|---|---|---|
| 1 | Blank group | 8 | 0 | Once a day, a total of 21 times/twice | Oral administration/ |
| 2 | Compound B | 8 | 5 | a week, a total of 6 times Once a day, a total of 21 times | Intraperitoneal injection Oral administration |
| 3 | Compound A | 8 | 3 | Twice a week, a total of 6 times | Intraperitoneal injection |
| 4 | Compound A/ Compound B | 8 | 5/3 | Once a day, a total of 21 times/twice a week, a total of 6 times | Oral administration/ Intraperitoneal injection |

The results of this experiment show that the efficacy of the combination of the PD-1 antibody (3 mpk) and famitinib malate (10 mpk) is superior to that of the PD-1 antibody or famitinib malate alone. The weight of mice in each group was normal, indicating that the drug had no obvious side effects.

Example 2: The Effect of Famitinib Malate on In Vitro Activity of TYRO3, AXL and MER Kinases (1) Experimental Procedures for IC50Profiler™

| Component | Concentration |
|---|---|
| Famitinib Malate | 1 nM-10 μM |
| MOPS buffer (pH 7.0) | 8 mM |
| EDTA | 0.2 mM |
| Peptide substrate | 250 μM |
| Magnesium acetate | 10 mM |
| [gamma-$^{33P}$]-ATP | 500 cpm/pmol |
| ATP | 10 μM |
| Kinase | Appropriate amount |

Note:
MOPS, 3-(N-morpholino) propanesulfonic acid

Appropriate amounts of kinase and peptide substrates were separately mixed with different concentrations of famitinib malate (1 nM, 3 nM, 10 nM, 30 nM, 100 nM, 300 nM, 1 μM, 3 μM, 10 μM) and incubated for 60 min at room temperature. Magnesium acetate and [gamma-33P]-ATP were added to initiate the kinase-catalyzed reaction, and the reaction was carried out at room temperature for 40 minutes. After the reaction was finished, 3% phosphoric acid solution was added to terminate the reaction. 10 μL of the reaction mixture was taken and added onto a P30 filter membrane to be filtered. The membrane was washed with 75 mM phosphate buffer for 3 times and washed once with methanol to remove free [gamma-33P]-ATP. The protein was fixed, and the membrane was dried. The liquid scintillation analyzer was used to determine the amount of peptide substrate by counting the amount of 33P.

(2) Test Results

According to the concentration-inhibition curve, the IC50 value resulting from fitting is shown in Table 1.

TABLE 1

| | Kinase | IC50 (nM) Famitinib Malate |
|---|---|---|
| 1 | Axl | 36.82 |
| 2 | Mer | 4.35 |
| 3 | TYRO3 (Rse) | 326.32 |

Example 3

1. Antibodies and Compounds to be Tested

Compound A: The heavy and light chain sequences thereof are as shown in SEQ ID NO: 7 and SEQ ID NO: 8 of present disclosure. 200 mg/each vial, formulated as 20 mg/ml for use;

Compound B: famitinib malate, which was prepared according to the method in patent application WO2007085188.

2. Enrollment Criteria: Patients with Advanced Kidney Cancer, Urothelial Cancer, Cervical Cancer, Recurrent Ovarian Cancer and Endometrial Cancer.

(1) For renal cell cancer: advanced renal clear cell cancer diagnosed by histology or cytology (tumor of mixed type, such as renal clear cell cancer as the dominant component, can be included in the group); the primary tumor has been surgically removed and has been treated with interleukin-2 and/or anti-angiogenesis targeting drugs, but the treatment failed;
   (2) For urothelial cancer: incurable urothelial cancer diagnosed by histology or cytology, including renal pelvic cancer, ureteral cancer, bladder cancer and urethral cancer. For cancer of mixed type, the main histological type should be transitional cell cancer subtype; the disease has progressed or relapsed after previous treatment of platinum-based regimens, with no more than 2 types of previously systemic treatment regimens.
   (3) For cervical cancer: advanced cervical squamous cell cancer diagnosed by histology or cytology; previously treated with ≥1 line systemic treatment but failed;
   (4) For recurrent ovarian cancer: recurrent ovarian epithelial cancer, fallopian tube cancer or primary peritoneal cancer diagnosed by histopathology, previously treated with platinum-based regimen, and the disease has progressed or relapsed during treatment, or less than 6 months after the treatment with platinum-based therapy (finished 4 or more courses of treatment);
   (5) For endometrial cancer: endometrial cancer diagnosed by histopathology, previously treated with at least platinum-based regimen, and the disease has progressed or relapsed after or during the treatment with therapy.

3. Dosing Regimen:

Compound A: intravenous injection, 200 mg, once every 3 weeks, 1 cycle every 3 weeks; Compound B: 20 mg or 15 mg, oral administration, once a day.

4. Safety Data

No drug-related death was observed when compound A was administered in combination with compound B. Although the incidence of grade 3 or higher grade adverse events was 60%, they were all controllable. Toxic reactions were mostly related to the administration of Compound B, which were effectively controlled by adjusting the regimen or suspending the administration of Compound B. The incidence of immune-related adverse events determined by the researchers was low (13.8%) and were substantially low-grade adverse events. Only one case was grade 3 acute enteritis, and the others were grade 2 or lower adverse events. In addition, when the two drugs were co-administered, only 2 subjects (2.5%) developed reactive cutaneous capillary hyperplasia, the incidence was significantly lower than that of compound A alone for the treatment of solid tumors (54.3%), suggesting that the adverse effects of compound A can be reduced by co-administration with Compound B. The overall incidence of serious adverse events was not high, and only 2 (2.5%) subjects withdrew from treatment due to SAE. For this reason, co-administration of Compound A and Compound B for the treatment of urinary system and gynecological tumors is safe.

5. Efficiency 75 cases out of the 80 subjects experienced at least one efficacy evaluation, and 5 subjects could not be evaluated due to withdrawal out or death before the first evaluation.

Among the 25 subjects in the kidney cancer cohort, 23 subjects were evaluated for efficacy. 12 subjects showed partial remission (PR), 9 subjects showed stable disease (SD), and 2 subjects showed disease progress (PD). The objective remission rate (ORR) was 52.2%, and the disease control rate (DCR) was 91.3%. The ORR was superior to that of Compound B 25 mg, q.d., alone for the treatment of kidney cancer (36%).

Among the 10 subjects in the urothelial cancer cohort, 9 subjects were evaluated for efficacy. 3 subjects showed partial remission (PR), 3 subjects showed stable disease (SD), and 3 subjects showed disease progress (PD). The objective remission rate (ORR) was 33.3%, and the disease control rate (DCR) was 66.7%.

24 subjects in the ovarian cancer cohort were evaluated for efficacy. 8 subjects showed partial remission (PR), 10 subjects showed stable disease (SD), and 7 subjects showed disease progress (PD). The objective remission rate (ORR) was 33.3%, and the disease control rate (DCR) was 75%.

Among the 5 subjects in the endometrial cancer cohort, 4 subjects were evaluated for efficacy. 2 subjects showed partial remission (PR), 1 subject showed stable disease (SD), and 1 subject showed disease progress (PD). The objective remission rate (ORR) was 50%, and the disease control rate (DCR) was 75%.

Among the 16 subjects in the cervical cancer cohort, 15 subjects were evaluated for efficacy. 8 subjects showed partial remission (PR), 5 subjects showed stable disease (SD), and 2 subjects showed disease progress (PD). The objective remission rate (ORR) was 53.3%, and the disease control rate (DCR) was 86.7%.

Overall, 75 cases out of 80 subjects experienced at least one efficacy evaluation, 33 subjects showed partial remission (PR), 27 subjects showed stable disease (SD), and 15 subjects showed disease progress (PD). The objective remission rate (ORR) was 44.0%, and the disease control rate (DCR) was 80.0%.

6. Pharmacokinetics

Among the 12 subjects who participated in the pharmacokinetic study, PK blood was collected from 9 subjects.

The results showed that the exposure amount of Compound B (when it was co-administrated with Compound A) was increased, when compared to the exposure amount of compound B administrated alone, and the PK parameters of compound B (including $C_{ss}$, min, $C_{ss}$, max, $AUC_{ss}$) were better than that when administrated alone.

TABLE 2

Pharmacokinetic Parameters of Compound B

| PK parameter (unit) | | Dose (administration alone) 20 mg (n = 8) | Dose (co-administration) 20 mg (n = 9) |
|---|---|---|---|
| $C_{ss, min}$ (ng/mL) | Mean ± SD | 33.2 ± 14.6 | 38.0 ± 11.0 |
| | Geomean (Geometric CV %) | 29.8 (56.6) | 36.6 (28.8) |
| $C_{ss, max}$ (ng/mL) | Mean ± SD | 64.3 ± 23.8 | 73.4 ± 16.8 |
| | Geomean (Geometric % CV) | 59.9 (44.4) | 71.6 (24.3) |
| $T_{ss, max}$ (h) | Median (Min, Max) | 6 (2, 8) | 6 (4, 10) |
| $AUC_{ss}$ (h*ng/mL) | Mean ± SD | 1185 ± 465 | 1356 ± 300 |
| | Geomean (Geometric % CV) | 1090 (48.5) | 1326 (23.2) |

Note:
Mean ± SD, mean ± standard deviation; Geomean, geometric mean.

7. Summary

For co-administration of Compound A and Compound B, the tolerance is favorable, the toxicity is controllable and tolerable. At the same time, co-administration can effectively reduce the occurrence of reactive capillary hyperplasia (a common adverse reaction caused by compound A) and provide favorable therapeutic effects.

---

What is claimed is:

1. A method of treating tumors in a patient in need thereof, the method comprising administering to the patient an anti-PD-1 antibody or antigen-binding fragment thereof and famitinib or a pharmaceutically acceptable salt thereof, wherein the light chain variable region of the PD-1 antibody comprises LCDR1, LCDR2 and LCDR3 as shown in SEQ ID NO: 4, SEQ ID NO: 5 and SEQ ID NO: 6 respectively, and the heavy chain variable region of the PD-1 antibody comprises HCDR1, HCDR2 and HCDR3 as shown in SEQ ID NO: 1, SEQ ID NO: 2 and SEQ ID NO: 3 respectively.

2. The method according to claim 1, wherein the PD-1 antibody is a humanized antibody.

3. The method according to claim 2, wherein the humanized antibody comprises a light chain variable region as shown in SEQ ID NO: 10 or variant thereof, and the variant has 0-10 amino acid change(s) on the light chain variable region of SEQ ID NO: 10; and the humanized antibody comprises a heavy chain variable region as shown in SEQ ID NO: 9 or variant thereof, and the variant has 0-10 amino acid change(s) on the heavy chain variable region of SEQ ID NO: 9.

4. The method according to claim 2, wherein the humanized antibody comprises a light chain as shown in SEQ ID NO: 8 or variant thereof, and the variant has 0-10 amino acid change(s) on the light chain variable region; and the humanized antibody comprises a heavy chain as shown in SEQ ID NO: 7 or variant thereof, and the variant has 0-10 amino acid change(s) on the heavy chain variable region.

5. The method according to claim 4, wherein the humanized antibody comprises a light chain as shown in SEQ ID NO: 8 and a heavy chain as shown in SEQ ID NO: 7.

6. The method according to claim 1, wherein the tumor is selected from the group consisting of breast cancer, lung cancer, liver cancer, gastric cancer, intestinal cancer, kidney cancer, urothelial cancer, cervical cancer, ovarian cancer, endometrial cancer, melanoma, non-small cell lung cancer and thyroid cancer.

7. The method according to claim 1, wherein the AUC of the famitinib or the pharmaceutically acceptable salt thereof is increased by at least 15%, when compared to that of the same dose of the famitinib or the pharmaceutically acceptable salt thereof administered alone.

8. The method according to claim 1, wherein the $C_{max}$ of the famitinib or the pharmaceutically acceptable salt thereof is increased by at least 15%, when compared to that of the same dose of the famitinib or the pharmaceutically acceptable salt thereof administered alone.

9. The method according to claim 1, wherein the PD-1 antibody or the antigen-binding fragment thereof is administered in a human subject at a dose of 10 mg to 300 mg, once every 2-3 weeks.

10. The method according to claim 1, wherein the famitinib or the pharmaceutically acceptable salt thereof is administered in a human subject at a dose of 0.1 mg to 100 mg, once a day.

11. The method according to claim 1, wherein the pharmaceutically acceptable salt of famitinib is malate.

12. The method according to claim 1, wherein the incidence of reactive capillary hyperplasia is no more than 15%, when compared to that caused by the same dose of the anti-PD-1 antibody administered alone.

13. A method for reducing adverse reaction(s) caused by an anti-PD-1 antibody or antigen-binding fragment thereof, the method comprising administering famitinib or a pharmaceutically acceptable salt thereof, in combination with the anti-PD-1 antibody as defined in claim 1 to a patient, and wherein the adverse reaction(s) is/are reactive capillary hyperplasia.

14. The method according to claim 13, wherein the incidence of the reactive capillary hyperplasia is no more than 15%.

15. A method for reducing the dose of a PD-1 antibody or antigen-binding fragment thereof, or the dose of famitinib or pharmaceutically acceptable salt thereof, when administrated alone, the method comprising administering the famitinib or the pharmaceutically acceptable salt thereof in combination with the PD-1 antibody as defined in claim 1 to a patient.

16. A pharmaceutical package, comprising famitinib or pharmaceutically acceptable salt thereof, and the PD-1 antibody or the antigen-binding fragment thereof as defined in claim 1.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Mus musculus

<400> SEQUENCE: 1

Ser Tyr Met Met Ser
1               5

<210> SEQ ID NO 2
<211> LENGTH: 17
<212> TYPE: PRT
<213> ORGANISM: Mus musculus

<400> SEQUENCE: 2

Thr Ile Ser Gly Gly Gly Ala Asn Thr Tyr Tyr Pro Asp Ser Val Lys
1               5                   10                  15

Gly

<210> SEQ ID NO 3
<211> LENGTH: 7
<212> TYPE: PRT
<213> ORGANISM: Mus musculus

<400> SEQUENCE: 3

Gln Leu Tyr Tyr Phe Asp Tyr
1               5

<210> SEQ ID NO 4
<211> LENGTH: 11
<212> TYPE: PRT
<213> ORGANISM: Mus musculus

<400> SEQUENCE: 4

Leu Ala Ser Gln Thr Ile Gly Thr Trp Leu Thr
1               5                   10

<210> SEQ ID NO 5
<211> LENGTH: 7
<212> TYPE: PRT
<213> ORGANISM: Mus musculus

<400> SEQUENCE: 5

Thr Ala Thr Ser Leu Ala Asp
1               5

<210> SEQ ID NO 6
<211> LENGTH: 9
<212> TYPE: PRT
<213> ORGANISM: Mus musculus

<400> SEQUENCE: 6

Gln Gln Val Tyr Ser Ile Pro Trp Thr
1               5
```

<210> SEQ ID NO 7
<211> LENGTH: 443
<212> TYPE: PRT
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(443)
<223> OTHER INFORMATION: heavy chain sequence

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Met Met Ser Trp Val Arg Gln Ala Pro Gly Lys Gly Leu Glu Trp Val
        35                  40                  45

Ala Thr Ile Ser Gly Gly Gly Ala Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Tyr Phe Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350
```

```
Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
            435                 440

<210> SEQ ID NO 8
<211> LENGTH: 214
<212> TYPE: PRT
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(214)
<223> OTHER INFORMATION: light chain sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Thr Trp Tyr Gln Gln Lys Pro Gly Lys Ala Pro Lys Leu Leu Ile
        35                  40                  45

Tyr Thr Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ile Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 116
<212> TYPE: PRT
```

```
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(116)
<223> OTHER INFORMATION: heavy chain variable region

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Met Met Ser Trp Val Arg Gln Ala Pro Gly Lys Gly Leu Glu Trp Val
        35                  40                  45

Ala Thr Ile Ser Gly Gly Gly Ala Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Tyr Phe Asp Tyr Trp Gly Gln Gly Thr Thr Val
            100                 105                 110

Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(107)
<223> OTHER INFORMATION: light chain variable region

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Thr Trp Tyr Gln Gln Lys Pro Gly Lys Ala Pro Lys Leu Leu Ile
        35                  40                  45

Tyr Thr Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ile Pro Trp
                85                  90                  95

Thr Phe Gly Gly Gly Thr Lys Val Glu Ile Lys
            100                 105
```